(12) United States Patent
Desai

(10) Patent No.: US 6,522,905 B2
(45) Date of Patent: *Feb. 18, 2003

(54) APPARATUS AND METHOD FOR CARDIAC ABLATION

(76) Inventor: Jawahar M. Desai, 8755 Petite Creek Way, Roseville, CA (US) 95661

(*) Notice: Subject to any disclaimer, the term of this patent is extended or adjusted under 35 U.S.C. 154(b) by 0 days.

This patent is subject to a terminal disclaimer.

(21) Appl. No.: 09/923,869

(22) Filed: Aug. 6, 2001

(65) Prior Publication Data

US 2002/0010392 A1 Jan. 24, 2002

Related U.S. Application Data

(63) Continuation of application No. 09/447,207, filed on Jan. 4, 2000, which is a continuation-in-part of application No. 08/029,771, filed on Mar. 11, 1993, now Pat. No. 5,433,198.

(51) Int. Cl.$^7$ .............................. A61B 5/0402
(52) U.S. Cl. ....................... 600/374; 607/122
(58) Field of Search ................... 606/41; 600/373–375, 600/515, 518, 523, 525; 607/115, 116, 119, 122, 125–128, 9, 14

(56) References Cited

U.S. PATENT DOCUMENTS

| 4,365,639 A | 12/1982 | Goldreyer |
| 4,649,924 A | 3/1987 | Taccardi |

(List continued on next page.)

FOREIGN PATENT DOCUMENTS

| EP | 0233731 A2 | 8/1987 |
| EP | 0481684 A2 | 4/1992 |
| EP | 0499491 A2 | 8/1992 |
| EP | 0573311 A1 | 12/1993 |
| WO | 8903657 | 5/1989 |
| WO | 9300958 | 1/1993 |
| WO | 9406349 | 3/1994 |
| WO | 9422366 | 10/1994 |

OTHER PUBLICATIONS

Calkins, Hugh, et al.; "Electrogram Criteria for Identification of Appropriate Target Sites for Radiofrequency Catheter Ablation of Accessory Atrioventricular Connections"; *Circulation*; vol. 85, No. 2; Feb., 1992; pp. 565–573.

Desai, Jawahar, et al.; "Endocardial Isochronal Patterns Near the Ventricular Tachycardia Site of Origin With Orthogonal Electrode Catheter Array"; *JACC*; vol. 13, No. 2; Feb., 1989; p. 167A (Abstract Only).

(List continued on next page.)

*Primary Examiner*—Jeffrey R. Jastrzab
(74) *Attorney, Agent, or Firm*—Skjerven Morrill LLP (57) ABSTRACT

A system and method for cardiac mapping and ablation include a multi-electrode catheter introduced percutaneously into a subject's heart and deployable adjacent to various endocardial sites. The electrodes are connectable to a mapping unit, an ablation power unit a pacing unit, all of which are under computer control. Intracardiac electrogram signals emanated from a tachycardia site of origin are detectable by the electrodes. Their arrival times are processed to generate various visual maps to provide real-time guidance for steering the catheter to the tachycardia site of origin. In another aspect, the system also include a physical imaging system which is capable of providing different imaged physical views of the catheter and the heart. These physical views are incorporated into the various visual maps to provide a more physical representation. once the electrodes are on top of the tachycardia site of origin, electrical energy is supplied by the ablation power unit to effect ablation.

15 Claims, 9 Drawing Sheets

U.S. PATENT DOCUMENTS

| | | | |
|---|---|---|---|
| 4,660,571 A | | 4/1987 | Hess et al. |
| 4,940,064 A | | 7/1990 | Desai |
| 5,154,501 A | | 10/1992 | Svenson et al. |
| 5,156,151 A | | 10/1992 | Imran |
| 5,158,092 A | | 10/1992 | Glace |
| 5,233,515 A | | 8/1993 | Cosman |
| 5,383,917 A | * | 1/1995 | Desai .................. 600/374 |
| 5,433,198 A | * | 7/1995 | Desai .................. 600/374 |
| 5,443,489 A | * | 8/1995 | Ben-Haim ............. 607/115 |
| 5,494,042 A | | 2/1996 | Panescu et al. |
| 5,657,755 A | * | 8/1997 | Desai .................. 600/374 |

OTHER PUBLICATIONS

Desai, Jawahar, et al.; "Orthogonal Electrode Catheter Array for Mapping of Endocardial Focal Site of Ventricular Activiation"; *PACE*; vol. 14; Apr., 1991; pp. 557–574.

Desai, Jawahar, et al.; "Two Phase Radiofrequency Ablation"; *Journal of Pacing and Clinical Electrophysiology*; vol. 14; Jul., 1991; pp. 1979–1987.

Downar, Eugene, et al.; "Intraoperative Electrical Ablation of Ventricular Arrhythmias: A 'Closed Heart' Procedure"; *JACC*; vol. 10, No. 5; Nov., 1987; pp. 1048–1056.

El–Sherif, Nabil, et al.; "Reentrant ventricular arrhythmias in the late myocardial infarction period"; *Circulation*; vol. 68, No. 3; Sep., 1983; pp. 644–656.

Fontaine, G., et al.; "Fulgaration of Chronic Ventricular Tachycardia: Results of Forty–Seven Consecutive Cases with a Follow–Up Ranging from 11 to 65 Months"; Chapter 106, pp. 978–985.

Haines, David E. and Denny D. Watson; "Tissue Heating During Radiofrequency Catheter Ablation: A Thermodynamic Model and Observations in Isolated Perfused and Superfused Canine Right Ventricular Free Wall"; *PACE*; vol. 12; Jun., 1989; pp. 962–976.

Harris, Louise, et al.; "Activation Sequence of Ventricular Tachycardia: Endocardial and Epicardial Mapping Studies in the Human Ventricle"; *JACC*; vol. 10, No. 5; Nov., 1987; pp. 1040–1047.

Huang, Shoei K. Stephen, et al., "Transcatheter High Energy Electrical Shock in Patients With Unimorphic Sustained Ventricular Tachycardia and Coronary Artery Disease"; *PACE*; vol. 12, NASPE Abstracts; Apr., 1989; pp. 674–675.

Ideker, Raymond, et al.; "The Assumptions of Isocharonal Cardiac Mapping"; *PACE*; vol. 12; Mar., 1989; pp. 456–478.

Jazayeri, Mohammad R., et al.; "Selective Transcatheter Ablation of the Fast and Slow Pathways Using Radiofrequency Energy in Patients With Atrioventricular Nodal Reentrant Tachycardia"; *Circulation*; vol. 85, No. 4; Apr., 1992; pp. 1318–1328.

Josephson, Mark E., et al.; "Recurrent Sustained Ventricular Tachycardia"; *Circulation*; vol. 57, No. 3; Mar., 1978; pp. 440–447.

Josephson, Mark E., et al., "Role of Catheter Mapping in the Preoperative Evaluation of Ventricular Tachycardia"; *The American Journal of Cardiology*; vol. 49; Jan., 1982; pp. 207–220.

Kadish, Alan H., et al.; "Vector mapping of myocardial activation"; *Circulation*; vol. 74, No. 3; Sep., 1986; pp. 603–615.

Langberg, Jonathan J., et al., ; "The Echo–Transponder Electrode Catheter: A New Method for Mapping the Left Ventricle"; *JACC*; vol. 12, No. 1; Jul., 1988; pp. 218–223.

Miller, John M., et al.; "Pattern of Endocardial Activation During Sustained Ventricular Tachycardia"; *JACC*; vol. 6, No. 6; Dec., 1985; pp. 1280–1287.

Morady, Fred, et al.; "Catheter ablation of ventricular tachycardia with intracardiac shocks: results in 33 patients"; *Circulation*; vol. 75, No. 5; May, 1987; pp. 1037–1049.

Robinson, Charles J.; "Medical Electronics"; *IEEE Spectrum*, Jan., 1991; pp. 76–78.

Simons, Sedgwick L. Jr.; "Make Fast and Simple Contour Plots on a Microcomputer"; *Byte Publications, Inc.*; Nov., 1983; pp. 487–492.

Smith, W.M., et al.; "Direct Cardiac Mapping"; *Cardiac Electrophysiology From Cell to Bedside.*; Zipes/Jalife Chapter 88; W.B. Saunders Company, Harcourt Brace Jovanovich, Inc.; 1990; pp. 849–858.

Spach, M.S., et al.; "Resolution of Discontinuous Versus Continuous Propagation: Microscopic Mapping of the Derivatives of Extracellular Potential Waveforms"; *Cardiac Electrophysiology From Cell to Bedside.*; Zipes/Jalife Chapter 16; W.B. Saunders Company, Harcourt Brace Jovanovich, Inc.; 1990; pp. 139–148.

* cited by examiner

APPARATUS AND METHOD FOR CARDIAC ABLATION

This application is a continuation of U.S. Ser. No. 09/447,207 filed Jan. 4, 2000, which is a Continuation-In-Part of application Ser. No. 08/029,771, filed Mar. 11, 1993 now U.S. Pat. No. 5,433,198.

BACKGROUND OF THE INVENTION

This invention relates to medical devices and, in particular, a system and technique of employing multi-electrode catheters for cardiac mapping and ablation.

Cardiac dysrhythmias are commonly known as irregular heart beats or racing heart. Two such heart rhythm irregularities are the Wolff-Parkinson-White syndrome and atrio-ventricular (AV) nodal reentrant tachycardia. These conditions are caused by an extraneous strand of conducting fibers in the heart that provides an abnormal short-circuit, pathway for electric impulses normally conducting in the heart. For example, in one type of Wolff-Parkinson-White syndrome the accessory pathway causes the electric impulses that normally travel from the upper to the lower chamber of the heart to be fed back to the upper chamber. Another common type of cardiac dysrhythmias is ventricular tachycardia (VT), which is a complication of a heart attack or reduction of blood supply to an area of heart muscle, and is a life threatening arrhythmia. All these types of dysrhythmias can usually be traced to one or more pathological "sites of origin" or tachycardia foci in the heart.

In the treatment of cardiac dysrhythmias, non-surgical procedures such as management with drugs are favored. However, some dysrhythmias of the heart are not treatable with drugs. These patients are then treated with either surgical resection of the site of origin or by Automatic implantable cardiovertor defibrillator (AICD). Both procedures have increased morbidity and mortality and are extremely expensive. Even AICD needs major surgical intervention. In addition, some patients of advanced age or illness cannot tolerate invasive surgery to excise tachycardia focus which causes dysrhythmias.

Techniques have been developed to locate sites of tachycardia and to disable their short-circuit function. The site of origin of tachycardia is determined by analysis of surface electrocardiogram or intracardiac electrogram signals during states of arrhythmias which may occur spontaneously or be induced by programmed pacing. Once the site of origin or focus is located, the cardiac tissues around the site are either ablated surgically or with electrical energy so as to interrupt abnormal conduction.

For cardiac mapping, several methods of gathering and analyzing surface electrocardiogram or intracardiac electrogram signals are commonly used.

Surface electrocardiogram is one tool in which the electrocardiograms are gathered from as many as twelve surface electrodes attached to various external body parts of a subject. The ensemble of electrocardiograms usually has a definite signature which may be matched to that generally established to associate with a site of origin in a given location of the heart. In this way, it is possible to determine the gross location of a tachycardia site in the heart.

Intracardiac electrogram allows a tachycardia site of focus to be located more accurately. It is obtained by detecting electrical signals within the heart by means of electrodes attached directly thereto.

Gallagher et al., "Techniques of Intraoperative ELectrophysiologic Mapping", *The American Journal of Cardiology*, volume 49, January 1982, pp. 221–240, disclose and review several methods of intraoperative mapping in which the heart is exposed by surgery and electrodes are attached directly to it. In one technique, the electrodes at one end of a roving catheter are placed on a series of epicardial or endocardial sites to obtain electrograms for mapping earliest site of activation with reference to surface electrocardiograms. For endocardial mapping, a cardiotomy may also be necessary to open the heart to gain access to the endocardium.

Gallagher et al., supra, also disclose a technique for simultaneous, global mapping of the external surface of the heart (epicardial mapping). A lattice of about 100 electrodes in the form of a sock is worn on the heart, thereby enabling multiple sites to be recorded simultaneously. This technique is particular useful for those cases where the ventricular tachycardia induced is unstable or polymorphic.

Global mapping by means of large array of electrodes has been further disclosed in the following two journal articles: Louise Harris, M.D., et al., "Activation Sequence of Ventricular Tachycardia: Endocardial and Epicardial Mapping Studies in the Human Ventricle," *Journal of American College of Cardiology (JACC)*, Vol. 10, November 1987, pp. 1040–1047; Eugene Downar, et al., "Intraoperative Electrical Ablation of Ventricular Arrhythmias: A "Closed Heart" Procedure," *JACC*, Vol. 10, No. 5, November 1987, pp. 1048–1056. For mapping the interior surface of the heart (endocardial mapping), a lattice of about 100 electrodes in the form of a inflatable balloon is placed inside the heart after cutting it open. Under some situations, a "closed heart" variation may be possible without the need for both a ventriculotomy and ventricular resection. For example, with the subject on cardiopulmonary bypass, a deflated balloon electrode array is introduced into the left ventricular cavity across the mitral valve. Once inside the ventricle, the balloon is inflated to have the electrodes thereon contacting the endocardium.

While the sock or balloon electrode arrays allow global mapping by acquiring electrogram signals over a wider area of the heart simultaneously, they can only be installed after open-chest surgery.

Catheter endocardial mapping is a technique for mapping the electrical signals inside the heart without the need for open-chest or open-heart surgery. It is a technique that typically involves percutaneously introducing an electrode catheter into the patient. The electrode catheter is passed through a blood vessel, like femoral vein or aorta and thence into an endocardial site such as the atrium or ventricle of the heart. A tachycardia is induced and a continuous, simultaneous recording made with a multichannel recorder while the electrode catheter is moved to different endocardial positions. When a tachycardia focus is located as indicated in intracardiac electrogram recordings, it is marked by means of a fluoroscope image. Catheter endocardial mapping are disclosed in the following papers:

M. E. Josephson and C. D. Gottlieb, et. al., "Ventricular Tachycardias Associated with Coronary Artery Disease," Chapter 63, pp. 571–580, *CARDIAC ELECTROPHYSIOLOGY—from cell to bedside*, D. P Zipes et al, Editors, W. B. Saunders, Philadephia, 1990.

M. E. Josephson et al., "Role of Catheter Mapping in the Preoperative Evaluation of Ventricular Tachycardia,"*The American Journal of Cardiology*, Vol. 49, January 1982, pp. 207–220. Linear multipolar electrode catheters are used in preoperative endocardial mapping.

F. Morady et. al., "Catheter Ablation of Ventricular Tachycardia With Intracardiac Shocks: Results in 33 Patients," *CIRCULATION*, Vol. 75, No. 5 May 1987, pp. 1037–1049.

Kadish et al., "Vector Mapping of Myocardial Activation," *CIRCULATION*, Vol. 74, No. 3, September 1986, pp. 603–615.

U.S. Pat. No. 4,940,064 to Desai discloses an orthogonal electrode catheter array (OECA). Desai et al., "Orthogonal Electrode Catheter Array for Mapping of Endocardiac Focal Site of Ventricular Activation," *PACE*, Vol. 14, April 1991, pp. 557–574. This journal article discloses the use of an orthogonal electrode catheter array for locating problem sites in a heart.

Upon locating a tachycardia focus, ablation of cardiac arrhythmias is typically performed by means of a standard electrode catheter. Electrical energy in the form of direct current or radiofrequency is used to create a lesion in the endocardiac tissues adjacent (i.e. underneath) the standard electrode catheter. By creating one or more lesions, the tachycardia focus may be turned into a region of necrotic tissue, thereby disabling any malfunctions.

Existing catheter mapping techniques typically rely on analysis of recorded electrograms. Locating the site of origin and tracking the whereabouts of the catheter are at best tricky and time-consuming, and often proved unsuccessful.

Thus, it is desirable, to have a catheter mapping and ablation system with precision and speed and able to provide comprehensive guidance on a real-time basis.

OBJECTS AND SUMMARY OF THE INVENTION

Accordingly, it is a general object of the present invention to treat ventricular tachycardia and other cardiac dysrhythmias by improved catheter mapping and ablations.

It is an object of the present invention to provide a system which is capable of rapid and accurate cardiac mapping.

It is another object of the present invention to provide a system which is capable of efficiently and accurately locating and ablating a site of origin of tachycardia.

It is another object of the present invention to provide accurate guidance for efficiently and accurately ablating an endocardial site by filling it with successive catheter ablations of a smaller area.

It is yet another object of the present invention to provide real-time visual maps indicating the relative positions of the electrodes, the tachycardia site of origin and the heart.

These and additional objects are accomplished by a system including a multi-electrode catheter selectively connectable to a mapping unit, an ablation unit and a pacing unit. The system also includes a computer for controlling the various functional components. In one embodiment the system additionally includes a physical imaging unit which is capable of providing different views of a physical image of the multi-electrode catheter percutaneously introduced into the heart of a subject.

Electrogram signals emanated from a tachycardia site of origin in the endocardium are detectable by the electrode array. Their arrival times are processed to generate various visual maps to provide real-time guidance for steering the catheter to the tachycardia site of origin.

In one embodiment, the visual map includes a footprint of the electrode array on an endocardial site. The arrival time registered at each electrode is displayed in association therewith. A medical practitioner can therefore steer the catheter in the direction of earlier and earlier arrival time until the tachycardia site of origin is located.

In another embodiment, the visual map also includes isochrones which are contours of equal arrival time. These isochrones are constructed by linear interpolation of arrival times registered at the electrode array and cover the area spanned by the electrode array. When the electrode array is far from the tachycardia site of origin, the isochrones are characterized by parallel contours. When the electrode array is close to or on top of the tachycardia site of origins, the isochrones are characterized by elliptical contours encircling the tachycardia site of origin. Therefore, the isochrones provide additional visual aid and confirmation for steering the catheter to the tachycardia site of origin.

In another preferred embodiment, the visual map also includes an estimated location of the tachycardia site of origin relative to the electrode array. This provides direct visual guidance for rapidly steering the catheter to the tachycardia site of origin. The tachycardia site of origin lies in the weighed direction of electrodes with the earliest arrival times. The distance is computed from the velocity and time of flight between the site of origin and a central electrode. The velocity is estimated from a local velocity computed from the inter-electrode spacings and arrival time differentials.

According to another aspect of the invention, the system also include a physical imaging system which is capable of providing different imaged physical views of the catheter and the heart. These physical views are incorporated into the various visual maps to provide a more physical representation.

In one embodiment, two visual maps display two views (e.g., x,y axes) of a physical image of the electrode array in the heart with a relative position for the tachycardia site of origin.

In another embodiment, a visual map display a three-dimensional perspective view of the electrode array in the heart with a relative position for the tachycardia site of origin.

In yet another embodiment, the visual map also marks previous sites or tracks visited by the electrode array.

With the aid of the visual maps, the electrode array can locate the tachycardia site of origin rapidly and accurately. The system then directs electrical energy from the ablation power unit to the electrode array to effect ablation.

Additional objects, features and advantages of the present invention will be understood from the following description of the preferred embodiments, which description should be taken in conjunction with the accompanying drawings.

DETAILED DESCRIPTION OF THE PREFERRED EMBODIMENTS

Figure 1:
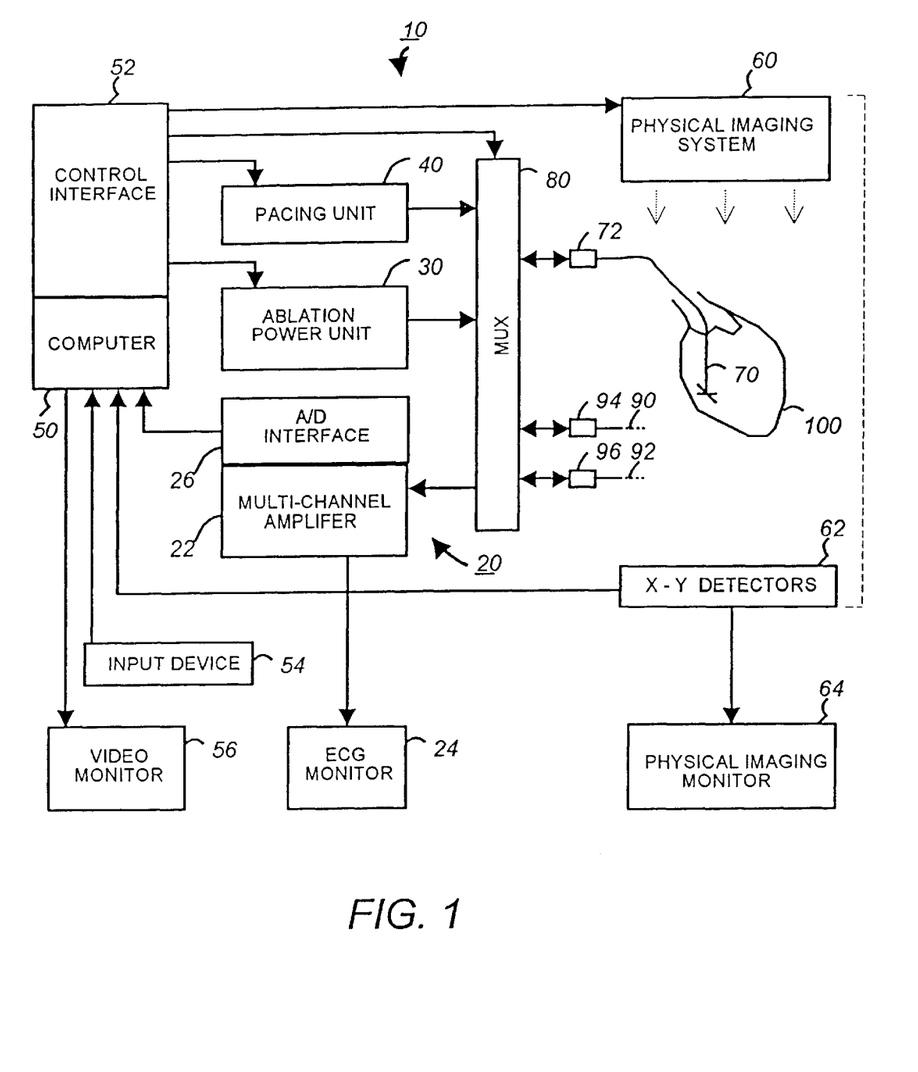
FIG. 1 is a schematic block diagram of a multi-electrode catheter mapping and ablation system of the invention.

FIG. 1 is a schematic block diagram of a multi-electrode catheter mapping and ablation system 10 according to a preferred embodiment of the present invention.

The system 10 essentially comprises of three functioning units, namely a mapping unit 20, an ablation unit 30 and a pacing unit 40. A computer 50 controls the operation of each of the units and their cooperations via a control interface 52. The computer receives operator inputs from an input device 54 such as a keyboard, a mouse and a control panel. The output of the computer may be displayed on a video monitor 56 or other output devices (not shown).

In the preferred embodiment the system 10 also includes a physical imaging system 60. The physical imaging system 60 is preferably a 2-axis fluoroscope or an ultrasonic imaging system. The physical imaging system 60 is controllable by the computer 50 via the control interface 52. In one implementation, the computer triggers the physical imaging system to take "snap-shot" pictures of the heart 100 of a patient (body not shown). The picture image is detected by a detector 62 along each axis of imaging. It usually includes a silhouette of the heart as well as inserted catheters and electrodes, and is displayed by a physical imaging monitor 64. Two monitors may be used to display the two images obtained along each of the dual axes. Alternatively, the two images may be displayed side-by-side on the same monitor. A digitized image data is also fed into the computer 50 for processing and integrating into computer graphics to be displayed on the video monitor 56.

A multi-electrode catheter 70 is selectively routed to each of the three functioning units 20, 30 and 40 via a catheter lead connector 72 to a multiplexor 80. Auxiliary catheters 90 or electrodes 92 are also connectable to the multiplexor 80 via one or more additional connectors such as 94, 96.

During cardial procedures, the multi-electrode catheter 70 is typically introduced percutaneously into the heart 100. The catheter is passed through a blood vessel (not shown), like femoral vein or aorta and thence into an endocardial site such as the atrium or ventricle of the heart. Similarly, auxiliary catheters 90 may also be introduced into the heart and/or additional surface electrodes 92 attached to the skin of the patient.

When the system 10 is operating in a mapping model, the multi-electrode catheter 70 as well as optional auxiliary catheters 90 function as detectors of intra-electrocardiac signals. The surface electrodes 92 serve as detectors of surface electrocardiogram signals. The analog signals obtained from these multi-electrode catheters and surface electrodes are routed by the multiplexor 80 to a multi-channel amplifier 22. The amplified signals are displayable by an electrocardiogram (EKG) monitor 24. The analog signals are also digitized via an A/D interface 26 and input into the computer 50 for data processing and graphical display. Further details of the data acquisition, analysis, and display relating to intracardiac mapping will be disclosed later.

When the system 10 is operating in an ablation mode, the multi-electrode catheter 70 is energized by the ablation unit 30 under the control of the computer 50. An operator issues a command through the input device 54 to the computer 50. The computer controls the ablation unit 30 through the control interface 52. This initiates a programmed series of electrical energy pulses to the endocardium via the catheter 70. A preferred implementation of the ablation method and device is disclosed in U.S. Pat. No. 5,383,917 by Desai, et al., the entire disclosure thereof is incorporated herein by reference.

When the system 10 is operating in a pacing mode, the multi-electrode catheter 70 is energized by the pacing unit 40 under the control of the computer 50. An operator issues a command through the input device 54 whereby the computer 50 controls through the control interface 52 and multiplexor 80 and initiates a programmed series of electrical simulating pulses to the endocardium via the catheter 70 or one of the auxiliary catheters 90. A preferred implementation of the pacing mode is disclosed in M. E. Josephson et al., "VENTRICULAR ENDOCARDIAL PACING II. The Role of Pace Mapping to Localize origin of Ventricular Tachycardia," *The American Journal of Cardiology*, Vol. 50, November 1982, relevant portion of the disclosure thereof is incorporated herein by reference.

In an alternative embodiment, the ablation unit 30 is not controlled by the computer 50 and is operated manually directly under operator control. Similarly, the pacing unit 40 may also be operated manually directly under operator control. The connections of the various components of the system 10 to the catheter 70, the auxiliary catheters 90 or surface electrodes 92 may also be switched manually via the multiplexor 80.

Mapping

An important advantage of the present invention is the capability of allowing a medical practitioner to use a roving catheter to locate the site of origin of tachycardia in the endocardium quickly and accurately, without the need for open-chest and open-heart surgery. This is accomplished by the use of the multi-electrode catheter 70 in combination with real-time data-processing and interactive display by the system 10.

Essentially, the multi-electrode catheter 70 must be able to deploy at least a two-dimensional array of electrodes against a site of the endocardium to be mapped. The intracardiac signals detected by each of the electrodes provide data sampling of the electrical activity in the local site spanned by the array of electrodes. This data is processed by the computer to produce a real-time display including arrival times of intracardiac signals at each electrode, and a local isochrone map of the sampled site. By plotting contours of equal arrival time of the intracardiac signals, the local isochrone map is an expedient way of indicating how close and where the electrode array is from the site of origin. Also, at each sampled site, the computer computes and displays in real-time an estimated location of the site of origin relative to the electrodes, so that a medical practitioner can interactively and quickly move the electrodes towards the site of origin.

A suitable multi-electrode catheter for use in the present invention is a five-electrode orthogonal electrode catheter array (OECA) that has been disclosed in U.S. Pat. No. 4,940,064 to Desai. Relevant portions of said disclosure are incorporated herein by reference.

Figure 2A:
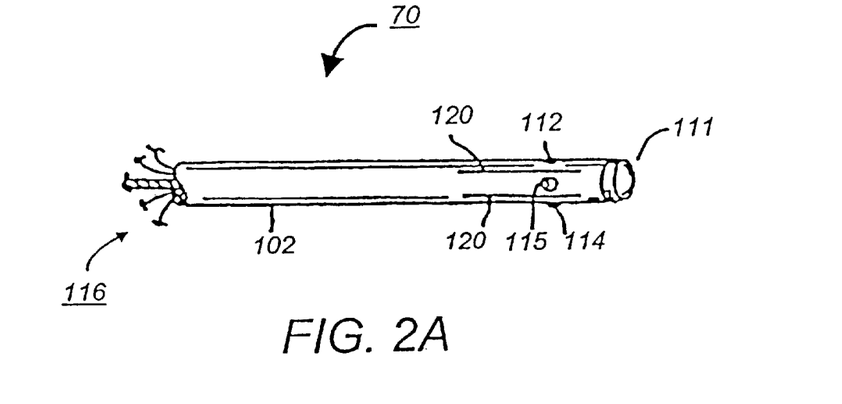
FIG. 2A illustrates the proximal end of the orthogonal electrode catheter array (OECA) in its fully retracted position or mode.

FIG. 2A illustrates the proximal end of the orthogonal electrode catheter array (OECA) 70 in its fully retracted position or mode. Because the catheter material has a "set" or "memory" it will normally return to this retracted position. The OECA comprises an eight-french five-pole electrode catheter 70. It has a central stylet 102 with four peripheral or circumferential electrodes 112, 113, 114 and 115. A fifth electrode 111 is located centrally at the tip of the stylet 102. All five electrodes are hemispherical and have individual leads 116 connected thereto. Each peripheral electrode is 2 mm in diameter while the central electrode is 2.7 mm in diameter. Slits 120 are cut longitudinally near where the electrodes are located.

Figure 2B:
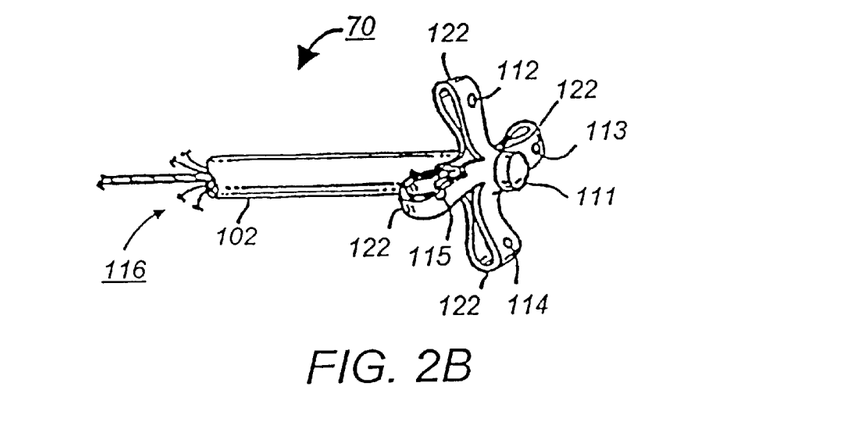
FIG. 2B illustrates the OECA in its fanned-out mode.

FIG. 2B illustrates the OECA in its fanned-out mode. When the proximal end (not shown) of the catheter is pulled, the stylet's slits 120 allow four side arms 122 to open from the stylet body in an orthogonal configuration. Each of the four arms 122 extend a peripheral electrode radially from the stylet so that the four peripheral electrodes forms a cross with the fifth electrode 111 at its center. The inter-electrode distance from the central electrode to each peripheral electrode is 0.5 cm, and the distance between peripheral electrodes is 0.7 cm. The surface area of the catheter tip in an open position is 0.8 $cm^2$.

Figure 2C:
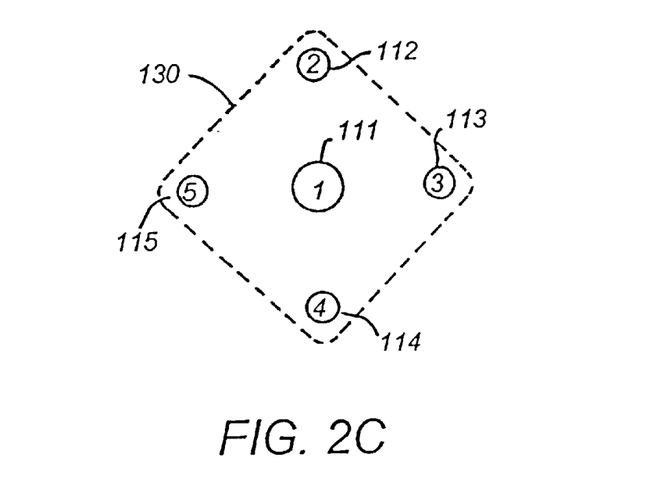
FIG. 2C shows the footprints of the five-electrode OECA electrodes.

FIG. 2C shows the footprints of the five-electrode OECA electrodes. The four peripheral electrodes 112, 113, 114 and 115 or (2)-(5) form a cross configuration. The fifth electrode 111 or (1) is located at the center of the cross. The orthogonal array of electrodes therefore provides five sampling points over the zone 130 in an endocardium site spanned by the electrodes.

Isochrone Maps

Generally when a patient's heart is in a state of tachycardia, the site of origin becomes the source of endocardial activation, emanating a series of activation wavefronts therefrom. Electrodes such as those deployed by the catheter 70 in the endocardium and located closer to the site of origin will detect these wavefronts earlier than those further away. The surface electrodes 92 being the furthest away from the site of origin will generally register latest wavefront arrival times.

When an endocardial site is being mapped by the OECA, a single measurement of an activation wavefront will provide arrival times at the five electrodes in real time. A local isochrone map for the sampled site can then be constructed from these arrival times, thereby showing contours of equal arrival times. The isochrones are readily computed by the computer using a linear interpolation scheme, as illustrated below.

Figure 3A:
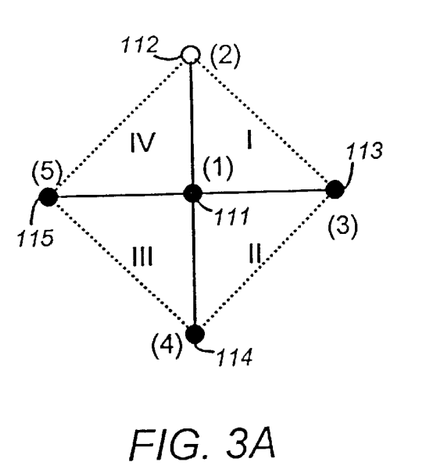
FIG. 3A illustrates the five electrodes of the OCEA positioned on a pair of orthogonal axes, each passing through a pair of peripheral electrodes and the central electrode.
Figure 3B:
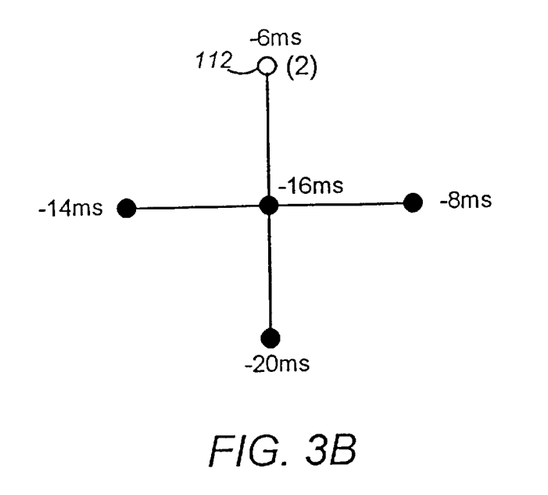
FIG. 3B shows an example measurement of the OECA from one endocardial site.

FIG. 3A illustrates the five electrodes of the OCEA positioned on a pair of orthogonal axes. Each orthogonal axes passes through a pair of peripheral, electrodes and the central electrode, viz 112-111-114 (or (2)-(1)-(4)) and 113-111-115 (or (3)-(1)-(5)). To implement the linear interpolation scheme, the zone spanned by the five electrodes is best divided into four triangular quadrants I to IV. Quadrant I is bounded by electrodes (1), (2), and (3). Quadrant II is bounded by electrodes (1), (3), and (4). Quadrant III is bounded by electrodes (1), (4), and (5). Quadrant IV is bounded by electrodes (1), (5), and (2). The local isochrones are then computed for each quadrant separately using linear interpolation along each side of the triangle FIG. 3B shows an example measurement of the OECA taken from one endocardial site. The five electrodes [(1), (2), (3), (4), (5)] each respectively has arrival time of [t(1), t(2), t(3), t(4), t(5)]=[−16, −6, −8, −20, −14] msec.

Figure 3C:
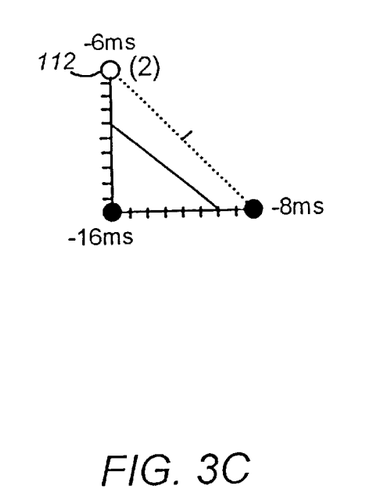
FIG. 3C illustrates the linear interpolation scheme applied to Quadrant I of the example shown in FIG. 3B.

FIG. 3C illustrates the linear interpolation scheme applied to Quadrant I of the example shown in FIG. 3B. Quadrant I is a triangle defined by the electrodes [(1), (2), (3)], each respectively having arrival times of [t(1), t(2), t(3)]=[−16, −6, −8] msec. Taking one millisecond steps, the side defined by electrodes (1) and (2) can be divided into ten equal steps from t=−6 to −16 msec. Similarly, the side defined by electrodes (2) and (3) can be divided into two equal steps from t=−6 to −8 msec, and the side defined by electrodes (1) and (3) can be divided into eight equal steps from t=−8 to −16 msec. Thus, an isochrone for the arrival time of −10 milliseconds can easily be drawn by joining a line from the −10 msec coordinate long each side. In this instance, the −10 msec, coordinate is found only along the two sides defined by electrodes (1) and (2) and electrodes (1) and (3).

Figure 3D:
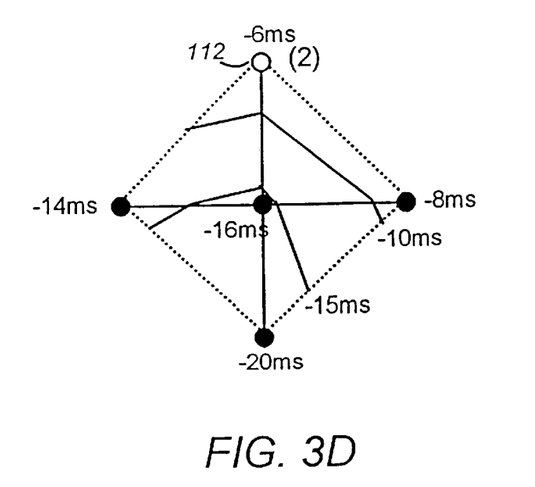
FIG. 3D shows the construction of a complete local isochronal map for the entire area cover by the OECA as shown in FIG. 3D.

FIG. 3D shows the construction of a complete local isochronal map for the entire area covered by the OECA. The complete local isochronal map is obtained by applying the linear interpolation method to all quadrants for all desired arrival times.

The activation wavefront arrival time at each electrode is measured relative to a reference time. The reference time is usually provided by the earliest deflection in a surface electrocardiogram which is monitored throughout the cardiac procedure.

Figure 4:
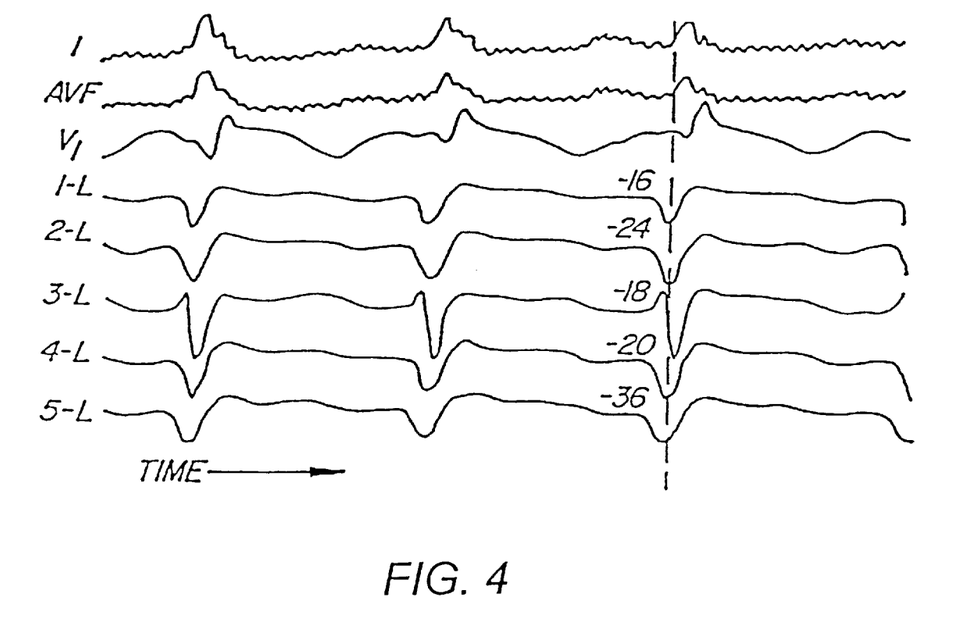
FIG. 4 shows example traces of surface EKG and intra-cardiac electrogram.

FIG. 4 shows typical example traces of surface EKG and intracardiac electrograms. The top three traces are three surface electrocardiograms I, AVF and V1, representing three planes (right to left, superior-inferior, anterior-posterior). These are continuously monitored and the earliest deflection on any of these electrocardiograms serves as a reference point of time. In this example, a perpendicular dotted line (reference time zero) is drawn from the earliest surface EKG which happens to be lead I. The next five traces are unipolar intracardiac electrograms as detected by an orthogonal electrode array catheter. It can been seen that electrode number 5, having the earliest arrival time of −36 msec is closer to the site of origin than the others.

It has been determined that an arrival time of −40 to −45 msec indicates that the detecting electrode is located substantially at the site of origin. In this case, the OECA yields a local isochrone map characterized by elliptical contours centered on the central electrode. On the other hand, when the OECA is substantially far away from the site of origin, its local isochrone map is characterized by parallel contours. The characteristic arrival time and associated isochronal signature are useful for locating the site of origin.

The intracardiac and surface EKGs are preferably digitized using a simple 8 or 16 channel signal digitizer. When the system 10 is in the mapping mode, the intracardiac electrograms and surface EKGs obtained from the multi-electrode catheter 70 and the surface electrodes 92 are digitized by the A/D interface 26. The digitized waveforms are analyzed by the computer to find the activation wavefront arrival times in real time.

The method of operation of the inventive system in mapping mode will now be described by way of an example as follows. The multi-electrode catheter 70 is first used in mapping. The catheter is inserted through the leg artery (right femoral) and advanced to the aortic arch and then to the left ventricle utilizing fluoroscopic guidance as provided by the physical imaging system 60.

Figure 5:
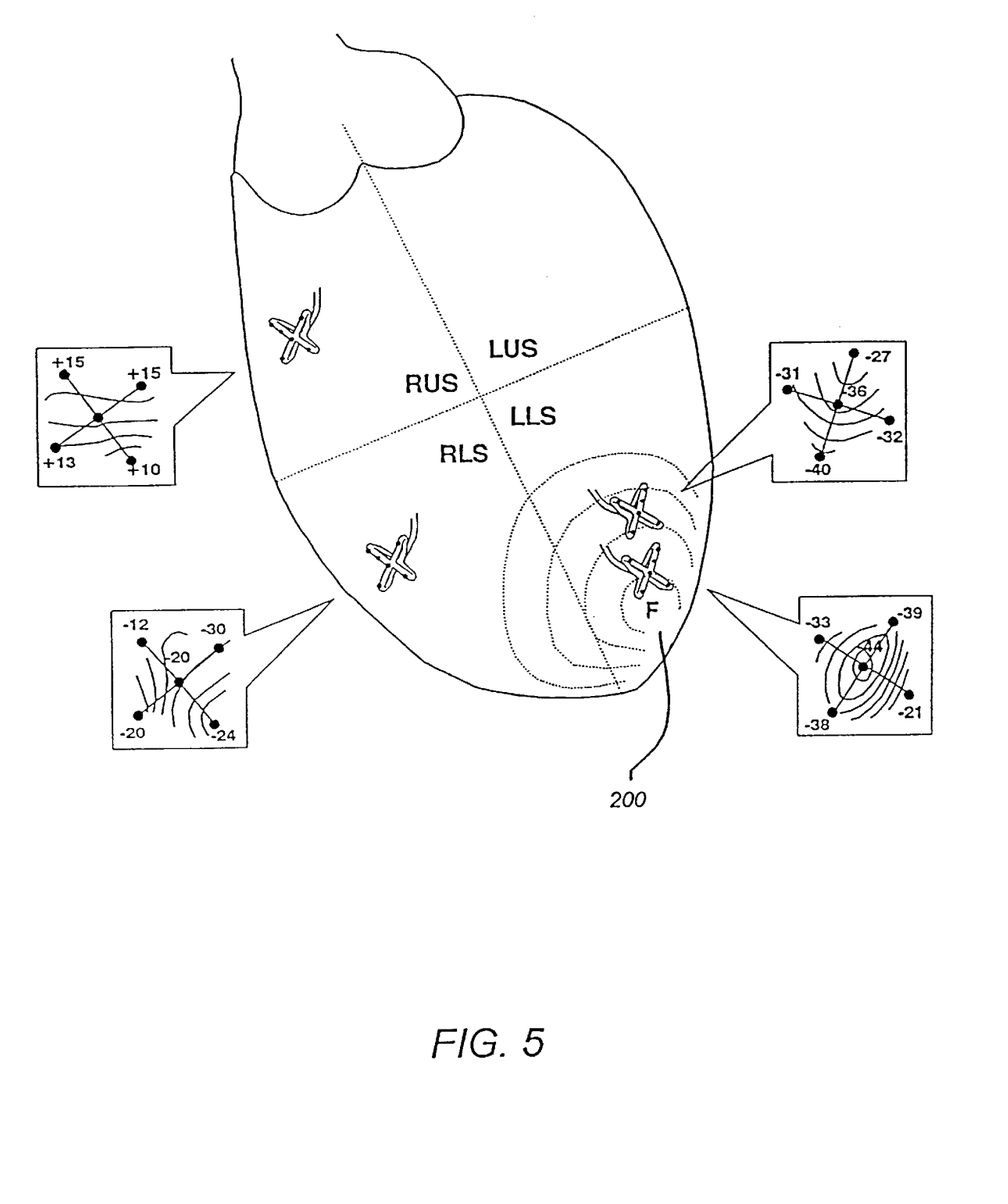
FIG. 5 illustrates schematically the ventricle or other heart chamber divided arbitrarily into four segments, and the isochrone maps obtained from various locations.

FIG. 5 illustrates schematically the ventricle or other heart chamber divided arbitrarily into four segments, right-upper (RUS) and right-lower (RLS), and left-upper (LUS) and left-lower (LLS) segments. In the example shown, a site of origin 200 is located in the (LLS) segment. The catheter 70 (OECA) is used to sample each of the segments in order to identify the segment containing the site of origin 200. The OECA is first positioned in the right upper segment, and its orthogonal electrode array is deployed to measure arrival times of wavefront activation from the site of origin. The system 10 is then instructed to initiate tachycardia by means of programmed electrical stimulation protocol from the pacing unit 40 to an electrode inserted into the endocardium. Once tachycardia is induced, the OECA picks up the intracardiac activation wavefront arrival times which are analyzed by the computer and a local isochrone map is displayed on the video monitor 56. In the example shown in FIG. 5, when the OECA is in the (RUS) segment, all electrodes register a rather late arrival time, which indicates that the site of origin is not in the (RUS) segment.

Next, the catheter electrodes are retracted and the catheter moved to the lower segment (RLS). In this way all four segments are mapped. In the example shown, the catheter is eventually repositioned in the segment (e.g., LLS) that demonstrates earliest arrival times.

Once the segment containing the site of origin has been identified, further manipulations of the catheter in that segment are undertaken with the interactive aid of the display on the video monitor 56. The display shows in real-time the local isochrone map, the electrode array and the estimated position of the site of origin relative thereto.

Figure 6A:
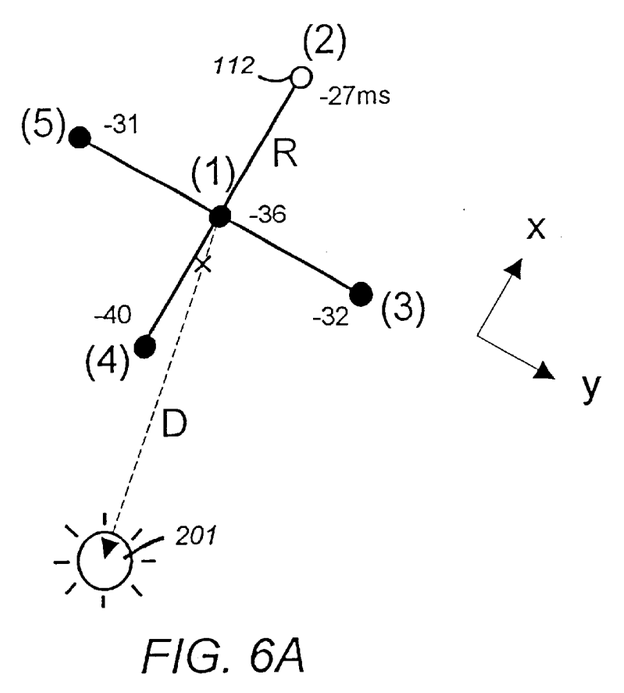
FIG. 6A illustrates by an example the construction of the displacement vector of the electrode array to the estimated site of origin.

FIG. 6A illustrates by an example the construction of the displacement vector of the electrode array to the estimated site of origin 201. Shown in FIG. 6A are the five electrodes of the OECA which are identical to the ones shown in FIG. 3A. The example shown has the five electrodes [(1), (2), (3), (4), (5)] each detecting an activation wavefront arrival time respectively of [t(1), t(2), t(3), t(4), t(5)]=[−36, −27, −32, −40, −31] msec. The orthogonal interelectrode spacing is R=5 mm in this case. As explained before, the goal is to locate the electrode array centrally about the actual site of origin. Since the site of origin is the source of the activation wavefronts an electrode located at the site will detect the earliest possible arrival time (typically −40 to 44 msec with respect to the first deflection of the surface EKG). The goal is achieved by having the central electrode (1) detecting the earliest possible arrival time. Conversely, when the electrode array is displaced from the site of origin, those electrodes further away from the site of origin will detect arrival times later (less negative) than those that are closer (more negative). Thus, the electrode array must be moved along the direction of more negative arrival time in order to close in on the site of origin.

According to one embodiment the direction in which the displacement vector joining the center of the electrode array to the estimated site of origin 201 is determined by linear interpolation of the respective arrival times detected at the five electrode locations. This can be easily performed by treating each arrival time as an "equivalent mass" located at each electrode and calculating the "center of mass" for the electrode array. The position of the "center of mass" is then given by:

$$[R_x, R_y] = \left[ \frac{\sum_i r_x(i)t_x(i)}{\sum_i t_x(i)}, \frac{\sum_j r_y(j)t_y(j)}{\sum_j t_y(j)} \right]. \quad (1)$$

The OECA conveniently defines a set of orthogonal axes with an (x,y) coordinate system, viz: the direction along electrodes (1)-(2) being the y-axis and the direction along electrodes (1)-(3) being the x-axis. The example data yield the position of the "center of mass" relative to the electrode (1):

$$[R_x, R_y] = \left[ \frac{-32 * R + (-31) * (-R)}{-32 + (-31)}, \frac{-27 * R + (-40) * (-R)}{-27 + (-40)} \right] \quad (2)$$
$$= [0.016, -0.19]R$$

where R=orthogonal interelectrode spacing (e.g. =5 mm).

The estimated site of origin 201 then lies along a direction D^ defined by a line through the central electrode (1) and the "center of mass", [$R_x, R_y$].

According to one aspect of the invention, the distance, |D|, between the central electrode (1) and the site of origin is estimated by first determining the local $$|D|=v_D|t(f)-t(1) \quad (3)$$

wavefront velocity, $v_D$, along the direction D^. Thus, where t(f)=arrival time measured at the site of origin, t(1)=arrival time measured at the central electrode (1).

In the case of the OECA, it is expediently accomplished by first computing the wavefront velocities along the x- and y-axis. This is estimated by the speed the wavefront travel from one electrode to another along the x- and y-axis:

$$[v_x, v_y] = \left[ \frac{R}{\Delta t_x}, \frac{R}{\Delta t_y} \right] \quad (4)$$

where R=interelectrode spacing, and the appropriate $\Delta t_x$, $\Delta t_y$ are given by the table below corresponding to the quadrant containing the direction D^:

| QUADRANT | $\Delta t_x$ | $\Delta t_y$ |
| --- | --- | --- |
| (1)-(2)-(3) | t(1)-t(3) | t(1)-t(2) |
| (1)-(3)-(4) | t(1)-t(3) | t(1)-t(4) |
| (1)-(4)-(5) | t(1)-t(5) | t(1)-t(4) |
| (1)-(2)-(5) | t(1)-t(5) | t(1)-t(2) |

The local wavefront velocity $v_D$ is estimated by adding the component of $v_x$ and $v_y$ along the direction D^, viz.:

$$v_D = v_x \cos\theta + v_y \sin\theta \quad (5)$$

where $\theta = \tan^{-1}(R_x/R_y)$ is the angle between D^ and the x-axis.

In the example given in FIG. 6A, the direction D^ lies within the quadrant (1)-(3)-(4). Then Equation (4) yields $$[v_x, v_y] = [1/-4, 1/4] R/ms$$

and Equation (5) yields $$v_D = 0.25\, R(-\cos\theta + \sin\theta)/\text{msec} \approx -0.25\, R/\text{msec}.$$

If the site of origin is assumed to have a measured arrival time of t(f)=−44 msec, then from Equation (3) the central electrode is displaced from the estimated site of origin 201 by a distance:

$$D = v_D(44-36) = 2R \text{ or } 10 \text{ mm}.$$

Figure 6B:
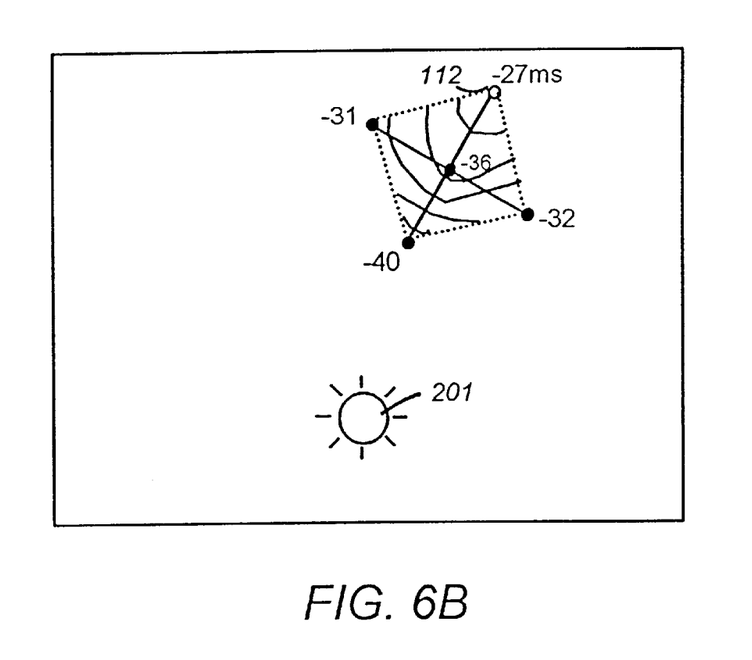
FIG. 6B is a display on the video monitor showing the relative positions of the electrode array and the estimated site of origin, according to a preferred embodiment of the invention.

FIG. 6B illustrates a computer graphical display on the video monitor 56 (see FIG. 1) in the preferred embodiment. The display shows, in real time and simultaneously, the electrode array with its local isochrone map and the relative position of the estimated site of origin 201. This greatly facilitates a medical practitioner to quickly steer the electrode catheter array to the site of origin. As the electrode catheter array is moved towards the estimated site of origin 201, the isochrones should be more and more elliptical. When the central electrode 111 is on top of the estimated site of origin, the isochrones should be ellipes wrapping around the central electrode 111. If this is not the case, t(f) needs to be revised and preferably changed in steps of 2 msec at a time, until the event when coincidence of the central electrode with the estimated site of origin is accompanied by elliptical isochrones wrapping around the central electrode.

As described earlier, Equation (1) is a linear interpolation scheme based on representing the arrival time at each electrode with an equivalent mass; the earlier the arrival time, the more "massive" it is. In this way, the data collected by every electrode in the array is taken into consideration. The equation as it stands is applicable if all the arrival time is negative, which is the case when the electrodes are not too far off-field from the site of origin. In general, to accommodate also positive or mixed positive and negative values of arrival times, it is expedient to shift all the arrival time values to the same polarity with the view of having the earliest arrival time represented by the largest value. In one embodiment, the arrival times are translated by the formulae $$t_x \to T_0 - t_x$$

$$t_y \to T_0 - t_y$$

where $T_0$ is a positive constant larger than any of the positive arrival time values. For example, $T_0 = 50$, and the calculation in Equation (2) yields $[R_x, R_y] \approx [1, -13]R$.

Figure 6C:
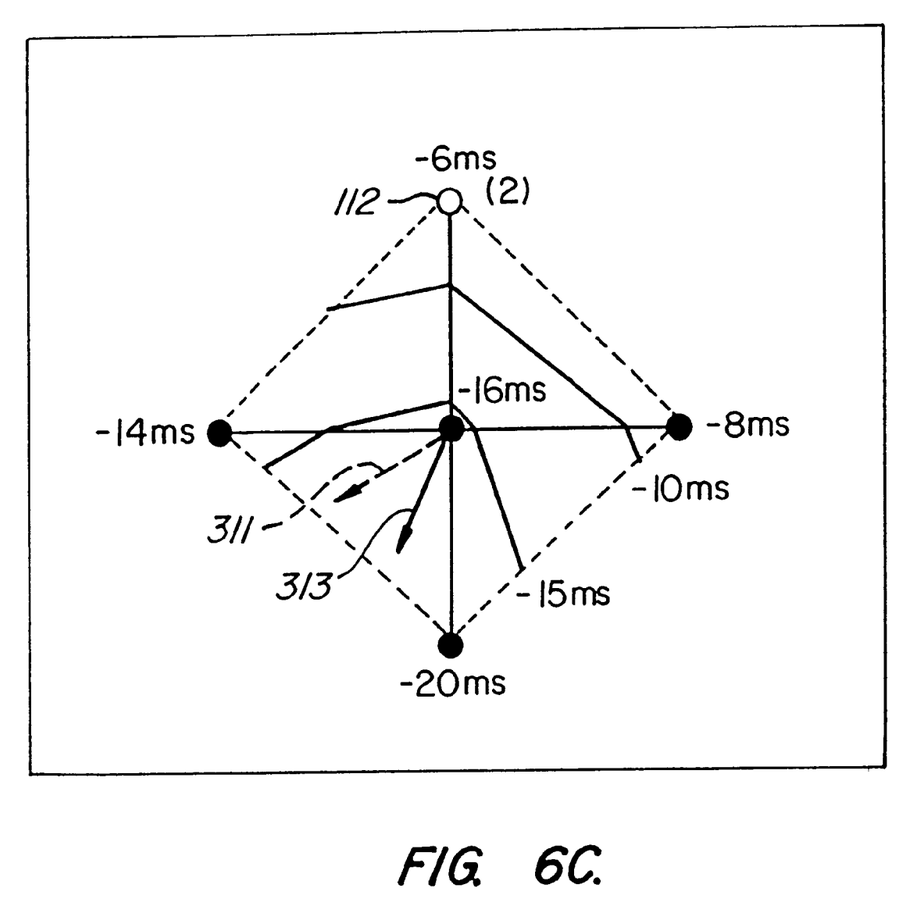
FIG. 6C illustrates a display according to another embodiment which includes the electrode array with the arrival times and the local isochrone map.

FIG. 6C illustrates a display according to another embodiment which includes the electrode array with the arrival times and the local isochrone map. In this embodiment, an arrow 313 indicates the estimated direction in which the catheter array should move in order to approach the site of origin. In general, as the catheter array is moved from site to site, there will be a map such as that illustrated in FIG. 6c associated with each site, with the current display showing the reading from the current site.

A further feature is the ability to store maps from previous sites and to recall these "history" information as needed. In one embodiment, another arrow 311 associated with the previous site is also displayed on the current map to provide a line of reference from the previous site. The previous arrow is displayed with a different attribute such as with broken line or with a different color in order to distinguish over the present arrow. In this way, the operator maneuvering the catheter will be able to tell whether the current catheter position is letting closer to the site of origin relative to the last one. In another embodiment, the previous map is display in a smaller window in one corner of the current map.

In yet another embodiment, as the catheter is mapping from site to site, the operator is able to mark the sites interactively on a graphical terminal. Typically, on the graphical terminal is displayed a schematic diagram of the heart such as the one shown in FIG. 5, and by reference to a flouoscopic image of the catheter in the heart, an operator can mark the equivalent site on the schematic diagram. Each marker on the schematic diagram is linked to its associated map or associated information. Subsequently, the operator is able to point to any existing marker and recall its associated map or information.

Physical Image Integration

The computer video display shown in FIG. 6B is constructed essentially from information obtained through data processing of wavefront arrival-time data sampled by the electrode catheter array 70. The display is an arrival-time field that exists in a two-dimensional space on the surface of the endocardium. For the purpose of locating the catheter at the site of origin, it provides adequate and cost-effective guidance.

According to another aspect of the invention, the information obtained by the physical imaging system 60 (see FIG. 1) is also integrated with the information obtained from the wavefront arrival-time data. The two types of information are synthesized by the computer 50, and are displayed on the video monitor 56 as a physical image of the heart 100 and showing therein the relative positions of the electrode catheter array 70 and the estimated site of origin 201. In this way a more physical representation of the catheter and heart is possible.

Figure 7A:
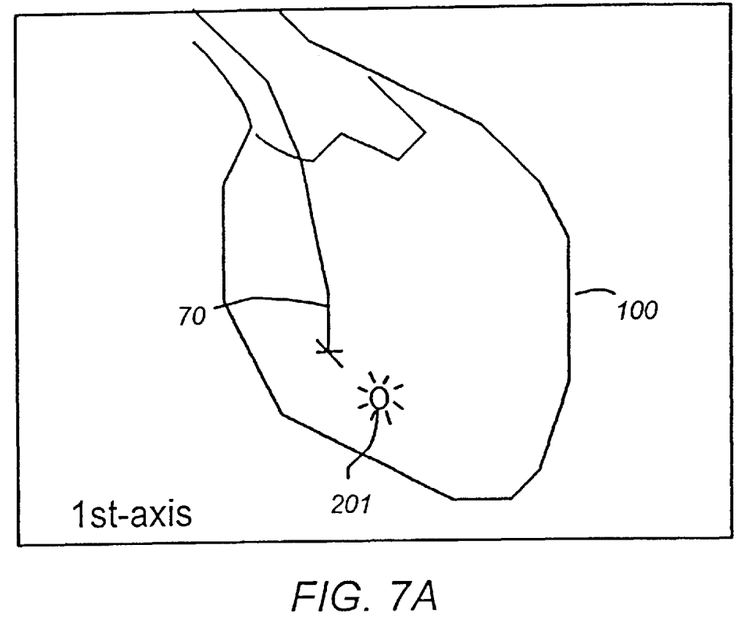
FIG. 7A is a synthesized display on the video monitor of a digitized picture of the heart and the electrode array therein taken along a first axis by the physical imaging system, and also showing the relative position of the estimated site of origin, according to another preferred embodiment of the invention.

FIG. 7A is a synthesized display on the video monitor of a digitized picture of the heart 100 and the electrode array 70 therein taken along a first axis by the physical imaging system, and also showing the relative position of the estimated site of origin 201, according to another preferred embodiment of the invention.

In one implementation, the physical imaging system 60 (also see FIG. 1) comprises two x-rays taken from two perpendicular directions. The video output of both x-ray machines is digitized, e.g., by using two separate video frame grabbers integrated into the x-y detectors 62. Since the electrode array 70 such as the OECA (also see FIGS. 2 and 3) has an x-ray opaque dart (not shown) on one of the electrode arms, it is relatively simple for the computer to properly identify each electrode and associate the correct arrival time with each electrode. In this way, the positions of the five electrodes of the OECA can be tracked by the computer 50 in real time.

The estimated site of origin 201 can be located by the method described earlier, except the coordinate system may be non-orthogonal, depending on the orientation of the electrode array.

Figure 7B:
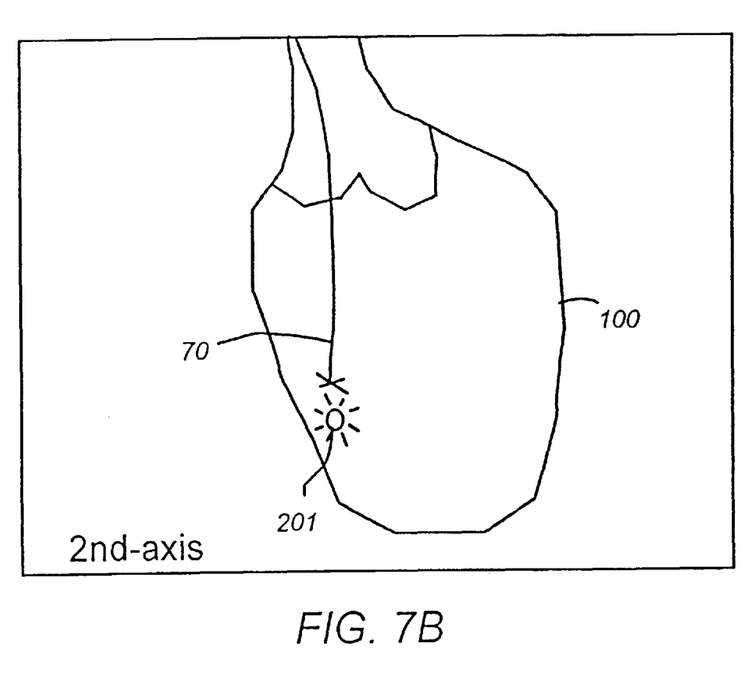
FIG. 7B is a display on the video monitor showing a similar picture as in FIG. 7A, but taken along a second axis by the physical imaging system.

FIG 7B is a display on the video monitor showing a similar picture as in FIG. 7A but taken along a second axis by the physical imaging system.

The views from the two axes may be displayed on two separated video monitors or on one monitor.

Figure 8:
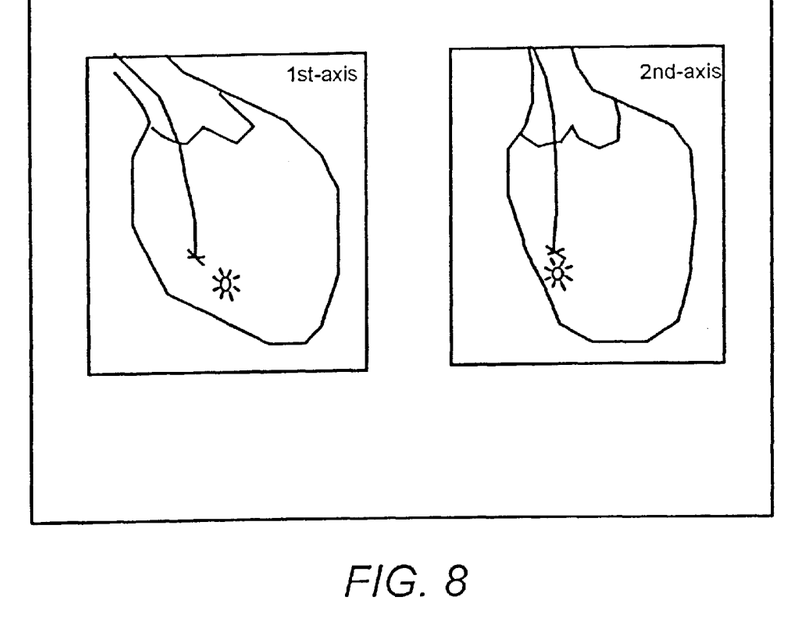
FIG. 8 is a display on the video monitor showing the pictures of FIGS. 7A and 7B simultaneously, according to another preferred embodiment of the invention.

FIG. 8 is a display on the video monitor showing the pictures of FIGS. 7A and 7B simultaneously, according to another preferred embodiment of the invention.

According to another embodiment of the invention, the video display is a perspective rendering of a three-dimensional image of the heart and the electrode array.

Figure 9:
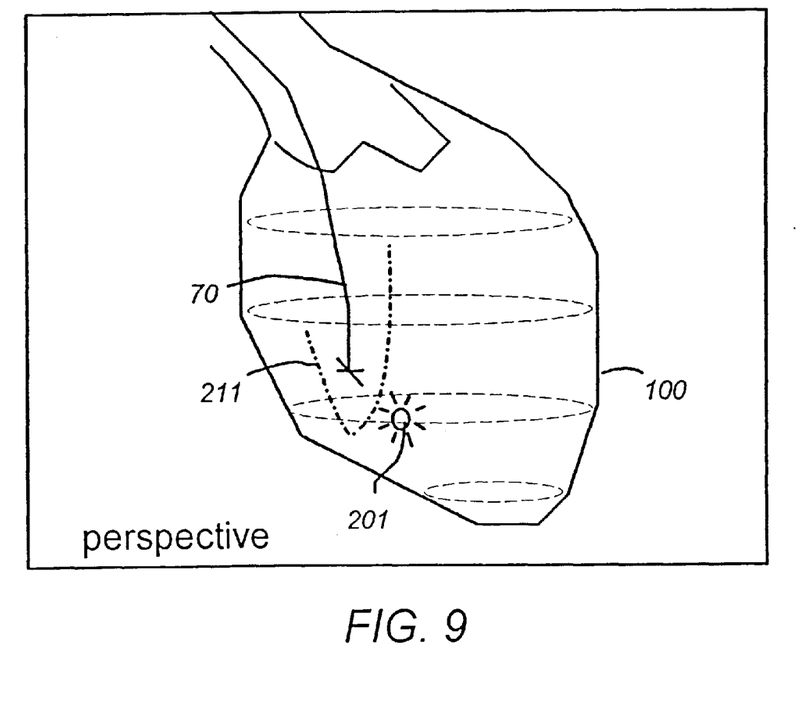
FIG. 9 is a display on the video monitor showing a relative position of the estimated site of origin against a perspective picture of the heart and the electrode array which is synthesized from pictures recorded from along several axes by the physical imaging system, according to another preferred embodiment of the invention.

FIG. 9 is a synthesized display on the video monitor of a perspective picture of the heart 100 and the electrode array 70 together with the estimated site of origin 201, according to another preferred embodiment of the invention. The image of heart 100 and the electrode array 70 are rendered from a three-dimensional image database which is collected from imaging along several axes by the physical imaging system. Each axis provide a view of the heart and the electrode array. The procedure for locating the estimated site of origin in each view is similar to that described before. The data gathered from the different views are processed by the computer to generate a three-dimensional perspective view. In one implementation, sites previously visited by the catheter 70 are also displayed as a track 211 in the endocardium.

The present inventive system is advantageous in allowing a medical practitioner to graphically track in real time the relative positions of the electrode array with respect to the heart and the estimated site of origin. Furthermore, it allows the possibility of accurate catheter positioning and repositioning in the endocardium and the possibility of tracking the history of the catheter previous positions.

Global Mapping

In preoperative studies and diagnosis or in medical research, a global mapping of the heart is valuable. A global isochronal map for the entire endocardium is assembled by the catheter scanning over the entire endocardium and the computer piecing together the local isochrone maps at each scanned site. The display includes tracks traversed by the catheter to provide guidance so that the endocardium can be mapped systematically. This will not only allow the computer to produce and display local isochronal maps in real time, but also separate isochronal maps of a larger area up to the whole endocardium by storing the actual positions of the electrodes for each measurement and the corresponding arrival times. As each additional measurement is taken, the (non-local) isochronal map could be updated to cover a larger area more accurately. This would allow the medical practitioner conducting a medical procedure to determine where to place the OECA next for measurement and to decide whether or not accurate enough isochronal map for the entire endocardium has been produced. Once an accurate enough isochronal map of the activation wavefront has been produced, a proper treatment procedure could then be determined.

Multi-Phase Radio Frequency Ablation

A preferred implementation of the ablation method and device is disclosed in copending and commonly assigned U.S. patent application Ser. No. 07/762,035 filed Jul. 5, 1991 by Desai, et al., the entire disclosure thereof is incorporated herein by reference.

After the site of origin is located by the electrode array, the system 10 (FIG. 1) is switched to the ablation mode. Electrical energy is transmitted from the ablation power unit 30 through the multiplexor 80 to the electrode array catheter 70. In the preferred embodiment, the ablation power unit 30 is programmable and under the control of the computer 50, so that a predetermined amount of electrical energy is delivered to ablate the endocardium.

In catheter ablation, the lesion formed is about the size of the energized electrode or electrode array. Conventional catheter ablation techniques have typically employed a catheter with a single electrode at its tip as one electrical pole. The other electrical pole is formed by a backplate in contact with a patient's external body part. These techniques have been used to disable the tachycardia site of origin in most cases. For example, it has been successfully used for the interruption or modification of conduction across the atrioventricular (AV) junction in AV nodal reentrant tachycardia; or for the interruption of accessory pathway in patients with tachycardia due to Wolff-Parkinson-White Syndrome; and for ablation in some patients with ventricular tachycardia (VT).

However, in ventricular tachycardia (VT), endocardial mapping with a standard electrode catheter can locate the exit site of ventricular tachycardia to within 4–8 cm$^2$ of the earliest site recorded by the catheter. A standard electrode catheter typically has a maximum electrode tip area of about 0.3 mm$^2$. Therefore, the lesion created by the simple RF technique delivered through a standard electrode catheter may not be large enough to ablate the ventricular tachycardia. Attempts to increase the size of lesion by regulation of power and duration by increasing the size of electrode or by regulating the temperature of tip electrode have met with partial success.

In order to increase the size of the lesion, the orthogonal electrode catheter array (OECA) with four peripheral electrodes and one central electrode provides a larger footprint. It typically produces a lesions of 1 cm$^2$.

However, in the ablative treatment of ventricular tachycardia (VT), lesion size of the order of more than one cm$^2$his probably required for effective treatment. In this case, a large lesion is formed by successive ablation of adjacent sites. For example, a larger lesion of 6 cm$^2$ size can be created by six adjacent square-shaped lesions of 1 cm$^2$. They can be formed by successive placements of the five-electrode OECA using RF energy. After each ablation, the electrode catheters is usually withdrawn to clean blood coagulum on the electrodes before the next attempt. It is critical that the locations of the next spot to be ablated as well as the reintroduced catheter must be known accurately and quickly for this procedure to be successful. This is accomplished by switching the system 10 alternately between the mapping and ablation mode. In the mapping mode, the system is preferably programmed to superposition a grid about the displayed tachycardia site such as that shown in FIG. 7, 8 or 9. The grid will enable accurate positioning of the electrode array.

While the embodiments of the various aspects of the present invention that have been described are the preferred implementation, those skilled in the art will understand that variation thereof may also be possible. The device and method described therein are applicable to ablation of biological tissues in general. Therefore, the invention is entitled to protection within the full scope of the appended claims.

What is claimed is:

1. A cardiac catheterization system for operation on an endocardium of a subject's heart, comprising:

a cluster of electrodes disposable by a catheter about the endocardium site-by-site; each electrode detecting intracardiac electrogram signals including that emanating from a tachycardia site of origin;

a storage for storing the detected intracardiac electorgram signals accumulated site-by-site;

a computer to derive from each said detected intracardiac electrogram signals an arrival time thereof and to form a map based on the arrival times derived from existing detected sites; and means for interactively displaying said map, said map including locations of existing detected sites and a current location of said cluster of electrodes, whereby those electrodes being closer to the tachycardia site of origin than others will be in a region of said map having earlier arrival times than others, and electrodes that are substantially coincident with the tachycardia site of origin will be in a region of said map having an earliest possible arrival time, thereby said map providing guidance for moving said cluster of electrodes towards the region having earlier arrival times.

2. A cardiac catheterization system as in claim 1, further comprising:

a power supply switchably supplying power to at least one of said cluster of electrodes when said at least one of said cluster of electrodes is placed substantially coincident with the tachycardia site of origin to ablate there at.

3. A cardiac catheterization system as in claim 2, wherein said power supply supplies radio frequency power of different phases to different electrodes among said cluster of electrodes.

4. A cardiac catheterization system as in claim 1, further comprising:

a physical imager displaying at least one view of a physical image of said cluster of electrodes relative to the heart.

5. A cardiac catheterization system as in claims 4, further comprising:

means for synthesizing said map with said at least one view from said physical imager to produce at least one synthesized video display showing at least one view of said physical image of said cluster of electrodes relative to the heart and an estimated tachycardia site of origin, thereby providing direct visual guidance for steering the cluster of electrodes to the tachycardia site of origin.

6. A cardiac catheterization system as in any one of claims 1–5, wherein said computer further computes contours of equal arrival time or isochrones; and said map includes isochrones computed from arrival times derived from existing detected sites.

7. A cardiac catheterization system as in any one of claims 1–5, wherein said map further includes an interactive track of said cluster of electrodes as it scans along a path on the endocardium.

8. A cardiac catheterization system for operation on an endocardium of a subject's heart, comprising:

a cluster of electrodes disposable by a catheter about the endocardium site-by-site; each electrode detecting intracardiac electrogram signals including that emanating from a tachycardia site of origin;

means for storing the detected intracardiac electorgram signals accumulated site-by-site;

means for deriving from each said detected intracardiac electrogram signals an arrival time thereof and to form a map based on the arrival times derived from existing detected sites; and means for interactively displaying said map, said map including locations of existing detected sites and a current location of said cluster of electrodes, whereby those electrodes being closer to the tachycardia site of origin than others will be in a region of said map having earlier arrival times than others, and electrodes that are substantially coincident with the tachycardia site of origin will be in a region of said map having an earliest possible arrival time, thereby said map providing guidance for moving said cluster of electrodes towards the region having earlier arrival times.

9. A method of cardiac catheterization for operation on an endocardium of a subject's heart, comprising:

disposing a cluster of electrodes of a catheter about the endocardium site-by-site; each electrode detecting intracardiac electrogram signals including that emanating from a tachycardia site of origin;

storing the detected intracardiac electorgram signals accumulated site-by-site;

deriving from each said detected intracardiac electrogram signals an arrival time thereof and to form a map based on the arrival times derived from existing detected sites; and interactively displaying said map, said map including locations of existing detected sites and a current location of said cluster of electrodes, whereby those electrodes being closer to the tachycardia site of origin than others will be in a region of said map having earlier arrival times than others, and electrodes that are substantially coincident with the tachycardia site of origin will be in a region of said map having an earliest possible arrival time, thereby said map providing guidance for moving said cluster of electrodes towards the region having earlier arrival times.

10. A method of cardiac catheterization as in claim 9, further comprising:

supplying power to at least one of said cluster of electrodes when said at least one of said cluster of electrodes is placed substantially coincident with the tachycardia site of origin to ablate there at.

11. A method of cardiac catheterization as in claim 10, wherein said power is in the form of radio frequency power of different phases being supplied to different electrodes among said cluster of electrodes.

12. A method of cardiac catheterization as in claim 9, further comprising:

physically imaging and displaying at least one view of a physical image of said cluster of electrodes relative to the heart.

13. A method of cardiac catheterization as in claim 12, further comprising:

synthesizing said map with said at least one view from said physical imager to produce at least one synthesized video display showing at least one view of said physical image of said cluster of electrodes relative to the heart and an estimated tachycardia site of origin, thereby providing direct visual guidance for steering the cluster of electrodes to the tachycardia site of origin.

14. A method of cardiac catheterization as in any one of claims 9–13, further comprising:

computing contours of equal arrival time or isochrones; and displaying said map with said isochrones computed from arrival times derived from existing detected sites.

15. A method of cardiac catheterization as in any one of claims 9–13, further comprising:

displaying said map with an interactive track as said cluster of electrodes is scanning along a path on the endocardium.

* * * * *